United States Patent [19]

Clewell et al.

[11] Patent Number: 4,631,259

[45] Date of Patent: Dec. 23, 1986

[54] TRANSPOSON IN CLONING DNA

[75] Inventors: Don B. Clewell; Mary C. Gawron-Burke, both of Ann Arbor, Mich.

[73] Assignee: Board of Regents of The University of Michigan, Ann Arbor, Mich.

[21] Appl. No.: 491,352

[22] Filed: May 4, 1983

[51] Int. Cl.[4] .................. C12P 21/00; C12N 1/00; C12N 15/00

[52] U.S. Cl. .................. 435/172.3; 435/68; 435/317; 935/23; 935/38; 935/56; 935/73

[58] Field of Search .............. 435/172.2, 172.3, 253, 435/832, 848, 885, 886

[56] References Cited

U.S. PATENT DOCUMENTS 4,237,224 5/1980 Cohen-Buyer ............. 435/172

OTHER PUBLICATIONS

Gawron-Burka et al., J Bact, vol. 159, pp. 214–221, 1984, "Regeneration of Insertionally Inactivated Streptococcal DNA Fragments After Excision of Tn916 in *Escherichia Coli*: A Strategy for Targeting ...".
Ike et al., J Bact, vol. 158, pp. 777–783, 1984, "Genetic Analysis of the PaD1 Pheromune Response in *Streptococcus Faecalis*, using Transposon Tn917 as an Insertional Mutagen".
Clewell et al., J Bact, vol. 152, pp. 1220–1230, "Mapping of *Streptococcus Faecalis* Plasmids pAD1 and pAP2 and Studies Relating to transposition of Tn917."
Clewell et al., J Bact, vol. 162(3), Jun. 1985, pp. 1212–1220, "*Streptococcus Faecalis* Sex Pheromone (CAM373) also produced by Staphyllococcus Aureus and Identification of a Conjugative Transposon (Tn918).
Bukhari et al., *DNA Insertion Elements, Plasmids and Episomes*, 1977, pp. 192–193, 210–211, 220–223, 226–227.
Ruvkun et al., *Nature*, vol. 289, Jan. 1981, pp. 85–89, "A General Method for Site-Directed Mutagenesir in Prokaryoter".
Donner et al., *Gene*, Apr. 1982, pp. 101–105, vol. 18, "Plasmid Cloning Vector Resistant to Ampicillin and Tetracycline Which Can Replicate in Both Hosts".
Morana et al., *Chem Abst.*, vol. 96, No. 11, 6868a, 1981, p. 173, "Molecular Cloning of the to1C locus of *Escherichia Coli* K-12 with the Use of Transposon Tn10".
Enger et al., *Diss Abst*, V. 42, (12P+1), No. 4678, 1981, "Excision and Transposition of Tn5 and Transposons".
Freifelder, *Molecular Biology*, 1982, pp. 770–777, Jones and Bartlett Publishers, Inc., Boston.
Starlinger, Peter, *Genetic Engineering to Biotechnology*, 1982, Edited W. J. Whelan and Sandra Black, Wiley & Sons, Ltd., "Transposable DNA Elements: What Can They Do and What Can We Do with Them?".
Smith et al., J. Bact., Oct. 1981, pp. 232–240, V. 145 (10), "Homology Among Tet Determinuntsr in Conjugative Elements of Streptococci".
Franke et al., J. Bact., Jan. 1981, pp. 494–502, V. 145 (1), "Evidence for a Chromosome-Borne Resistane Transposon (Tn916) in *Streptococcus faecalis* That is Capable of Conjugal Transfer."

Primary Examiner—Thomas G. Wiseman
Assistant Examiner—Robin Lyn Teskin
Attorney, Agent, or Firm—Peter F. Casella; James F. Dautremont

[57] ABSTRACT

Processes and new genetic materials are provided for cloning specific DNA fragments by using a unique conjugative transposon designated Tn916. The transposon is used to first target specific genes by insertional inactivation. A restriction fragment containing the inserted transposon is then inserted into a plasmid vector and transformed into *Escherichia coli* or other suitable host by selection for the transposon encoded tetracycline (Tc) resistance. The transformants so produced are then grown in the absence of tetracycline conditions under which Tn916 excises from the chimeric plasmid thus restoring the integrity of the DNA into which the transposon was originally inserted. This process provides a new and useful way of producing new life forms that are useful for making desired products having established utility.

8 Claims, 4 Drawing Figures

TRANSPOSON IN CLONING DNA

The development of this invention was supported by a grant from the National Institutes of Health.

BACKGROUND OF THE INVENTION

There are a multitude of schemes that have been reported and are currently used for the cloning of DNA. (See for example, Molecular Cloning A Laboratory Manual by T. Maniatis, E. Fritsch and J. Sambrook, Cold Spring Harbor Laboratory Publications, Cold Spring Harbour Laboratory, Box 100, Cold Spring Harbor, N.Y.) Most of these processes depend on techniques that do not select for a specific DNA fragment unless that fragment happens to already have a selectable marker. Thus, once a mixture of restriction fragments are ligated to a specific vector and transformed into a recipient bacterium, hundreds and perhaps thousands of transformants must then be screened to identify the clone of interest. This random, or shot gun approach as it is referred to, is very time consuming. The only other way to clone a specific fragment of DNA that does not have a selectable genetic marker on it requires that the fragment must be relatively pure prior to cloning. However, it would also be a very time consuming process to identify and purify the specific fragment. A further disadvantage of current cloning techniques becomes evident when DNA from a Gram positive bacterium, such as *Bacillus subtilis* is being cloned into *E. coli*, a Gram negative bacterium. In this case, there is the possibility that the desired genetic information encoded in the cloned fragment will not be expressed and thus can only be screened for by hybridization to specific probes. If expression does occur, but involves proteins that are normally excreted or located on the cell surface of the Gram positive bacterium, subsequent passage through the Gram negative cell envelope may not be possible.

There are four types of vector systems generally used to clone fragments of DNA into *E. coli*. They are plasmids, bacteriophage λ, cosmids and bacteriophage M13. Each vector system has particular features which make them useful for different purposes. They also share several common features. They can replicate autonomously in *E. coli*, they can be easily separated from bacterial nucleic acids and purified, and they contain regions of DNA that are not essential for propagation and into which foreign DNA can be inserted.

Cloning in plasmid vectors exemplified by Cohen/Boyer in U.S. Pat. No. 4,237,224, is in principle strightforward. The plasmid DNA is cleaved with a restriction endonculease and joined in vitro to foreign DNA. The recombinant plasmids that result, are then used to transform bacteria. In practice the plasmid vector must be chosen carefully for the particular cloning experiment in order to minimize the effort necessary to identify and characterize the DNA fragment of interest. The major difficulty is to distinguish between plasmids that contain the DNA fragment of interest from those that contain other pieces of foreign DNA and plasmid vectors that have recircularized.

The use of bacteriophage λ as a cloning vector was first demonstrated by N. E. Murray and K. Murray, (see Nature, 251: 476, 1974) and A. Rambach and P. Tiollais (see Proc. Nat. Acad. Sci., 71: 3927, 1974) Cloning with bacteriophage involves several steps. The bacteriophage vector DNA is digested with the appropriate restriction enzyme and ligated to fragments of foreign DNA having compatible termini. The resulting recombinant DNA's are packaged in vitro into viable bacteriophage particles that form plaques on the appropriate hosts. Recombinant phages carrying the desired foreign DNA are identified by procedures involving nucleic acid hybridization. There is no single bacteriophage λ vector suitable for cloning all DNA fragments. It is therefore necessary to choose carefully among the various bacteriophage vectors for the one best suited.

Cosmids were first developed by Collins and Hohn (see Proc. Nat. Acad. Sci., 75: 4242, 1978) and are vectors specifically designed for cloning large fragments of eukaryotic DNA. The essential components of cosmids are a drug resistance marker, plasmid origin of replication, one or more restriction sites for cloning, a DNA fragment that contains the ligated cohesive end (cos) site of bacteriophage λ, and a small size. A number of technical problems have prevented the wide spread use of this cloning technique. These problems, namely vector to vector ligation, "scrambling", and difficulties in screening large numbers of bacterial colonies can be dealt with using some recent advances by Meyerowitz et al. (see Gene 11: 271, 1980) and Grosveld et al. (see Gene 13: 220, 1981) Overall, the use of cosmids is most useful for certain specialized purposes such as isolation of large genes or for so called chromosome walking experiments.

The primary advantage of using bacteriophage M13 as a cloning vector is that the phage particles released from the cell contain single stranded DNA and therefore can be sequenced by the Sanger dideoxy-sequencing method (see Sanger et al. Proc. Nat. Acad. Sci., 74: 5463, 1977). However the relative instability of DNA inserts larger than about one kilobase effectively eliminates the usefulness of single stranded bacteriophages like M13 for most cloning purposes.

Transposons are discrete mobile DNA segments that are common constituents of plasmid, virus, and bacterial chromosomes. These elements are detected by their ability to transpose self encoded phenotypic traits from one replicon to another, or to transpose to a known gene and inactivate it. There are two types of transposons and they range in size from about 750 to greater than 50,000 nucleotide base pairs. One type known as the small insertion sequence or IS element are usually detected and were first discovered in the late 1960's as unusual insertion mutations. They do not encode any known phenotypic traits. The other type are relatively large units that do encode phenotypic traits such as antibiotic resistance. They were discovered in the mid 1970's. (See Plasmids and Transposons Environmental Effects and Maintenance Mechanisms; Edited by C. Stuttard and K. Rozee; Academic Press, New York; Pages 165-205)

Tn916 is a 10 megadalton transposable DNA element encoding resistance to tetracycline (Tc). It was originally identified on the chromosome of *Streptococcus faecalis* strain DS16 and is described in detail in Franke and Clewell, J. Bacteriol., 145: 494, (1981). Tn916 is unique because in addition to its ability to transpose into various plasmids, it has been shown to have fertility properties (Franke and Clewell J. Bacteriol., 145: 494, 1981 and Gawron-Burke and Clewell, Nature, 300: 281, 1982). Tn916 also has the unique property of readily excising under non selective conditions in an *E. coli* host.

BRIEF DESCRIPTION OF THE INVENTION

The invention relates to a simple and time saving method for cloning specific DNA fragments by using a unique transposon designated Tn916. This invention also relates to the new genetic materials thereby produced. The transposon is first used to target specific genes by insertional inactivation. We have found that Tn916 inserts into the DNA of a given recipient by conjugation or transformation. A restriction fragment containing the insertion is then cloned into an appropriate plasmid vector in E. coli, or other suitable host by selection for the transposon-encoded tetracycline resistance. The transformants are subsequently grown under nonselective conditions which results in Tn916 excising from the chimeric plasmid, restoring the integrity of the DNA into which the transposon was originally inserted. The new life forms which result are then employed to carry out new functions such as producing products of known utility.

THE FIGURES AND THE TABLES

Table 1 summarizes results of Tn916 transfer from plasmid free donors the plasmid free recipients.

Table 2 illustrates the segregation of erythromycin and tetracycline resistance in filter matings involving CG180 donors.

Figure 1:
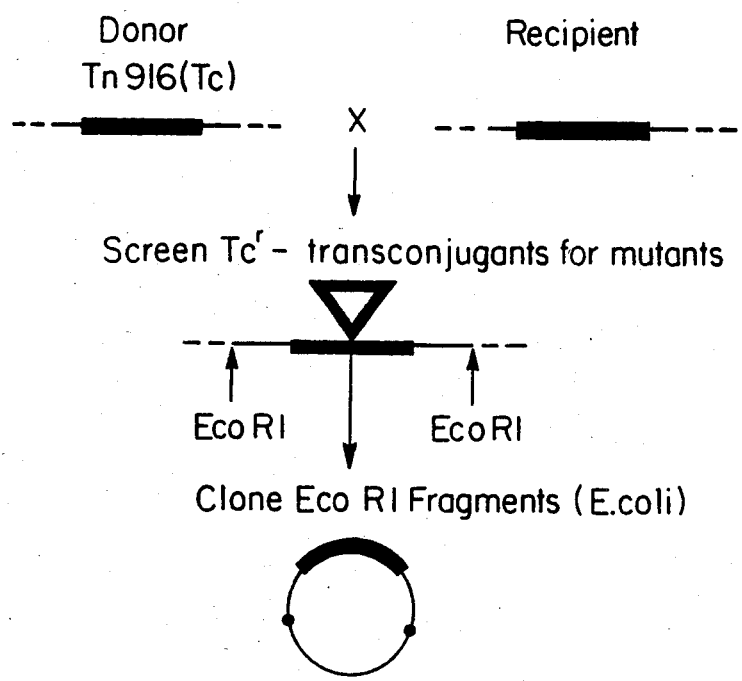
FIG. 1 is a diagrammatic sketch illustrating the process of this invention which is presented so that this invention may be more readily understood in connection with the explanation given later.

Referring to FIG. 1 and in accordance with our invention, Tn916 contained in the donor is introduced into the recipient via conjugation and the tetracycline resistant recipients are screened for mutational defects. EcoR1 fragments from recipient DNA are then cloned into E. coli.

Figure 2:
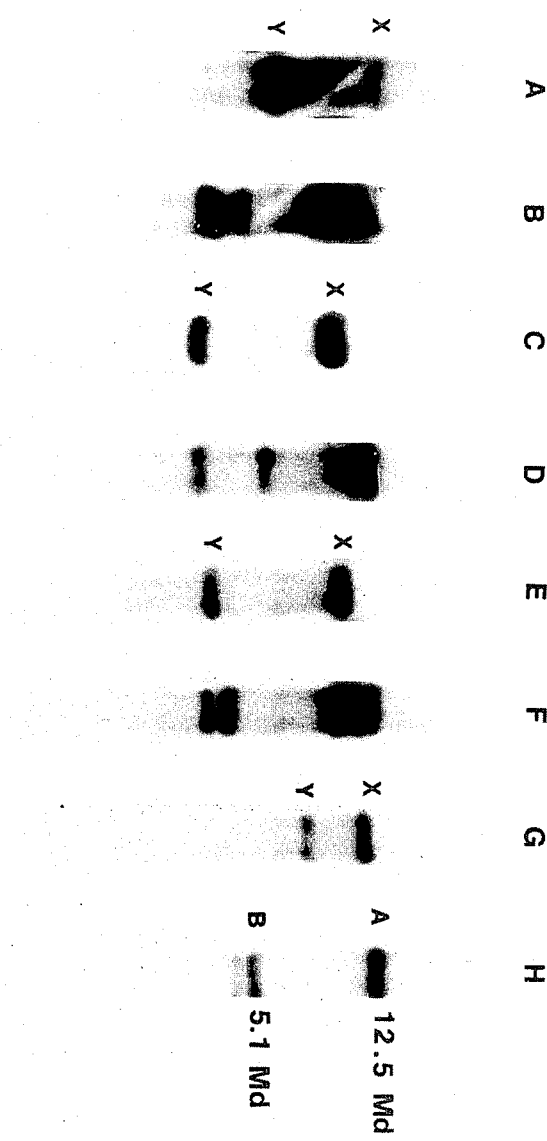
FIG. 2 is an autoradiogram obtained from filter blot hybridization analysis of chromosomal DNA from tetracycline resistant transconjugants.

Referring to FIG. 2, HindIII digested DNA (1-2 ug) from transconjugants CG110, CG140, and CG130, (lanes B-D respectively) which were obtained using DS16C3 (lane A) as donor. Lanes E-G contain HindIII digested DNA from transconjugants CG131, CG132, and CG133, respectively, which were obtained using CG130 as donor. Fragments marked X and Y denote chromosome-transposon junction fragments. Lane H contains HindIII digested pAM211 DNA and hybridizing bands are approximately 18.5 and 7.5 kilobases respectively.

Figure 3:
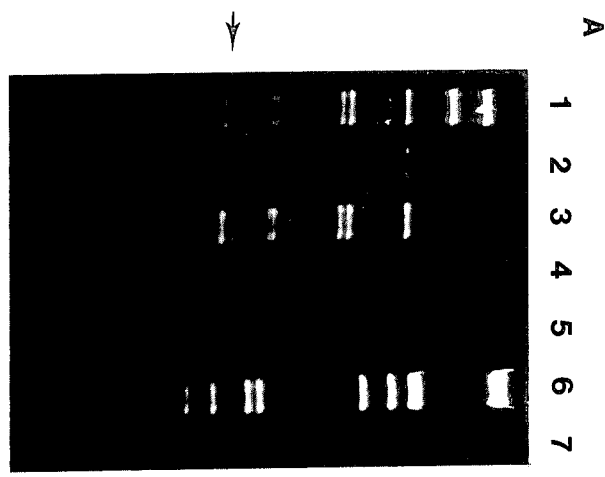
FIG. 3 is an agarose electrophoresis analysis of the structural integrity of plasmid DNA sequences in various transconjugants showing excision of Tn916 after transfer to recipients.
Figure 3:
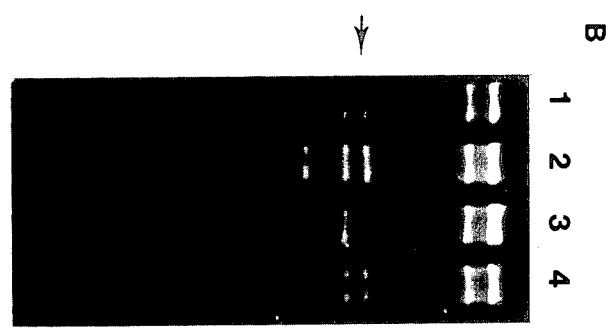

Referring to FIG. 3, HindIII digests of transconjugant plasmid DNAs derived from the CG180 donor. Lanes A1 and A2 contain plasmid DNA from CG180 and CG130(pAM81), respectively. The arrow marks fragment G, no longer present after Tn916 insertion into pAM81. Lanes A3-A5 contain plasmid DNA from the erythromycin/tetracycline resistant transconjugants CG184 and CG186, and the erythromycin/tetracycline resistant transconjugant CG187. Lane A7 contains plasmid DNA from the erythromycin/tetracycline resistant CG181 strain, and lane A6 contains DNA digested with EcoR1 and HindIII. Lanes B1-B4 contain plasmid DNA from the erythromycin/tetracycline transconjugants CG191 and CG194. The restriction pattern obtained for pAM190 is identical to that of CG193. The arrow marks the EcoR1 fragment D of pAD1, lost as a result of Tn916 insertion and dregenerated after excision.

Figure 4:
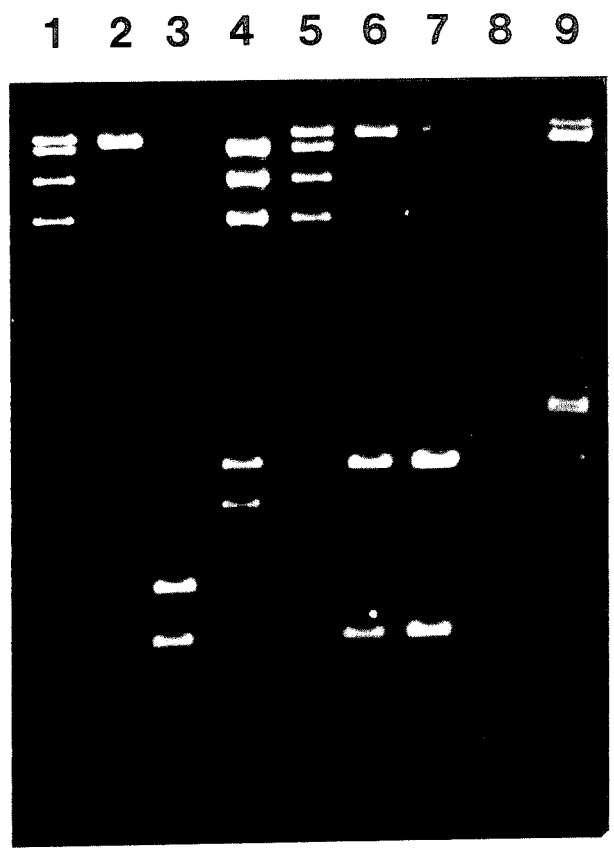
FIG. 4 illustrates the excision of Tn916 which occurs readily in the absence of selective pressure in the E. coli background.

Referring to FIG. 4, agarose gel electrophoresis of EcoR1 digested chimeric plasmid DNAs isolated from tetracycline/ampicillin resistant transformants of E. coli DH1 subsequently grown in the presence or absence of tetracycline. EcoR1 fragments by convention are labeled alphabetically in order of decreasing size (from top to bottom). Lanes 1-4 contain plasmid from strains OG1RF (pAM211), CG120 grown in 2.5 ug/ml tetracycline, CG120Lt grown without drug, and strain DS16C2 (which contains the plasmid pAD1), respectively. Lanes 5-7 involve plasmid DNAs from the analogous experiment which cloned the EcoR1 D' fragment of the plasmid pAM210 into which Tn916 had inserted. Lane 8 contains plasmid DNA from strain 101 (pGL101) and lane 9 conains lambda DNA digested with EcoR1 and HindIII.

DETAILED DESCRIPTION OF THE INVENTION

The process of this invention employs a novel transposon, Tn916 which encodes tetracycline resistance. We have found that Tn916 is able to insert into the DNA of a given recipient by conjugation or transformation; when done by conjugation a filter mating is carried out using, for example, S. faecalis strain DS16C3 or CG110 as the donor. DS16C3is a plasmid-free derivative of DS16 and CG110 is a derivative of JH2-2 harboring several copies of Tn916 in its chromosome. CG110 has the advantage of being able to donate Tn916 about 100 fold better than DS16C3. The mating procedures are described in Gawron-Burke and Clewell, Nature, 300: 281, 1982 and Franke and Clewell, J. Bacteriol., 145: 494, 1981.

In the case where transformation is used, DNA consisting of a plasmid vector containing Tn916 (such as pAM118) can be introduced into a transformable recipient such as Streptococcus sanguis (Macrina et al., Gene, 19: 345, 1982). Studies have shown that upon transformation, Tn916 is excised and inserts into the recipient chromosome as explained later.

The process of cloning specific fragments of DNA using Tn916 comprises the following sequence of steps.

1. Tetracycline-resistant transconjugants (or transformants) are screened for defective or altered function in the specific gene of interest (within the DNA restriction fragment to be cloned).

2. The bacteria containing the insertionally inactivated gene fragment to be cloned are separated from the mixture of transconjugants.

3. The DNA containing the Tn916 insertionally inactivated gene fragment to be cloned is isolated from the bacteria obtained in step #2.

4. The DNA is restricted with a restriction enzyme that leaves Tn916 intact (EcoR1, Sal1, BamH1 for example).

5. The restriction product of step #4 is ligated to a vector.

6. The product of step #5 is transformed into E. coli or other suitable host and selected for tetracycline resistance.

7. The product of step #6 is grown in the absence of tetracycline to excise Tn916 and reform the inactivated gene.

INSERTION OF Tn916 INTO RECIPIENT GENOME

The ability of Tn916 to transfer from plasmid-free donors in overnight filter matings is shown in the data of Table 1. DS16C3 is able to transfer tetracycline resistance at a frequency of about $10^{-8}$ to the plasmid-free recipient strain JH2-2. Transconjugants such as CG130 are capable of transferring tetracycline resistance to the isogenic recipient JH2SS at a similar frequency. FIG. 2 shows that when HindIII cleaved chromosomal DNA from three different transconjugants obtained from the DS16C3×JH2-2 mating, (detailed in Table 1) were probed with P32 labeled DNA containing Tn916, the hybridization patterns (lanes B through D) were different from those seen in the donor (lane A) as well as from each other (there is a single HindIII site within Tn916). One such transconjugant, CG140, gave rise to two chromosome-transposon junction fragments (X and Y), whereas two other transconjugants, CG110 and CG130, gave rise to four or more bands. FIG. 2 shows the hybridization profiles of transconjugants derived from the secondary mating described in Table 1 that had used strain CG130 as the donor. Again the hybridization bands of the transconjugants (lanes E through G) differred from those of the donor as well as from each other. Strain CG132 gave rise to a multiple band pattern, whereas two other transconjugant strains, CG131 and CG133, exhibited the simpler banding pattern.

TABLE 1

Tn916 Transfer From Plasmid-Free Donors

| Donor Strain | Recipient Strain | Frequency of Tc$^r$ Transconjugants Per Recipients | Representative Transconjugants |
|---|---|---|---|
| DS16C3 | JH2-2 | $1 \times 10^{-8}$ | CG110 |
|  |  |  | CG130 |
|  |  |  | CG140 |
| CG130 | JH2SS | $2 \times 10^{-8}$ | CG131 |
|  |  |  | CG132 |
|  |  |  | CG133 |
| CG110 | JH2SS | $4 \times 10^{-6}$ |  |

The variation in hybridization profiles among different trnsconjugants implies that Tn916 inserts at different sites on the recipient chromosome. In addition other hybridization experiments involving EcoR1 digestion of chromosomal DNA have revealed the presence of non-tandem multiple copies of the entire transposon in strains CG110, CG130, and CG132.

Methods for the screening of specific genetic defects resulting from the insertion of Tn916 will vary greatly and depend on the particular gene of interest, and such methods are known (see for example Advanced Bacterial Genetics, Cold Spring Harbor Laboratory, Cold Spring Harbor, N.Y. 1980). Once the specific insertionally inactivated transconjugants are isolated, the DNA from the bacteria is isolated, restricted with the appropriate restriction endonuclease, ligated to a vector, and introduced into E. coli or some other host bacteria. The materials and techniques used to carry out these steps are the subject of many books and scientific publications. For details see Principles of Gene Manipulation of R. W. Old and S. B. Primrose 1981, University of California Press.

EXCISION OF Tn916 AND REFORMATION OF THE INSERTIONALLY INACTIVATED FRAGMENT

During filter matings of S. faecalis involving conjugative plasmids into which Tn916 had been inserted, the transposon was found to excise at relatively high frequency upon transfer to a recipient strain (Gawron-Burke and Clewell, Nature, 300: 281, 1982). pAM180 is a derivative of the 26 kilobase erythromycin-resistance plasmid pAM81 with Tn916 inserted into the HindIII fragment G. When donor strains containing pAM180 were filter-mated with JH2SS, a high degree of segregation of the erythromycin and tetracycline resistance determinants occurred, as can be seen in the data of Table 2. Although both the erythromycin and tetracycline resistance determinants transferred at similar frequencies, a significant proportion of erythromycin selected transconjugants (43-77%) were not resistant to tetracycline.

Of those transconjugants selected for tetracycline resistance, however, greater than 90% were also erythromycin resistant. Interestingly, in some of the erythromycin selected transconjugants that were tetracycline resistant erythromycin and tetracycline resistance were no longer linked, as implied by a great reduction in the transfer frequency of tetracycline resistance but not erythromycin resistance in secondary matings. The segregation of the tetracycline resistance determinant from the plasmid is believed to relate to a zygotic induction of one or more Tn916-related recombination enzymes.

To determine the structural integrity of pAM81 DNA sequences in the various types of transconjugant, DNA from representative plasmids was digested with HindIII and analysed by agarose gel electrophoresis (FIG. 3).

TABLE 2

Segregation of Em$^r$ and Tc$^r$ in Filter Matings Involving CG180 Donors

| | Em$^r$ Tc$^r$ Transconjugants | | |
|---|---|---|---|
| Experiment | Erythromycin Selected | Tetracycline Selected | Erythromycin Selected Em$^r$ Tc$^r$ Transconjugants With Unlinked Markers |
| 1 | 27/47(57%) | 41/43(95%) | 6/12 |
| 2 | 16/48(33%) | 46/48(96%) | 1/12 |
| 3 | 11/48(23%) | 44/48(92%) | 1/10 |

Plasmid DNA isolated from two erythromycin/tetracycline resistant transconjugants in which erythromycin and tetracycline were no longer linked (CG184 and CG186) exhibit a restriction pattern identical to that seen for pAM81. (Note the two fragments of pAM180 that had contained Tn916 sequences were lost, and pAM81 fragment G reappeared). It is presumed that Tn916 transposed to the bacterial chromosome in these strains since they were tetracycline resistant and capable of transferring Tn916 at very low frequency. Plasmid DNA from strain CG187 (erythromycin/tetracycline resistant) also gave rise to a restriction pattern identical to that of pAM81. In constrast, plasmid DNA from strain CG181 (erythromycin/tetracycline resistant) in which both resistance determinants remained linked, displayed a restriction pattern identical to that of the pAM180 donor. These data suport the view that transposition involves an excision followed by insertion, but the insertion is not necessarily coupled to excision in which case the excised element is lost.

Analogous results were obtained in matings that used as a donor strain CG190. This strain harbors a pAD1 derivative (pAM190) with two transposon insertions: Tn917 harboring erythromycin resistance and Tn916; insertion of the latter causes failure to express hemolysin. CG190 transferred erythromycin resistance at a frequency of $2 \times 10^{-4}$ per donor to JH2-2 in overnight broth matings; and tetracycline sensitive derivatives (for example CG191) as well as tetracycline resistant derivatives in which the erythromycin and tetracycline resistance determinants were no longer linked (CG194 were found among the transconjugants at a frequency of about 4%. Agarose gel electrophoresis of EcoR1 digested plasmid DNA from such transconjugants (FIG. 3) revealed the presence of a fragment (EcoR1 D fragment) that had been missing in the original pAM190 DNA as a result of Tn916 insertion. Most significant was the additional observation that transconjugants CG191, CG192, and CG194 all regained the hemolytic phenotype, implying that the excision of Tn916 was precise. Transconjugants in which the erythromycin and tetracycline resistance markers remained linked, such as CG193, displayed an EcoR1 restriction pattern like the donor and were, as expected, nonhemolytic.

Excision is also evident when plasmid DNA containing Tn916 is introduced directly into the transformable S. sanguis strain Challis. The plasmid pAM118 is a derivative of the E. coli-Streptococcus shuttle plasmid pVA838 (Macrina et al. Gene, 19: 345, 1982) and contains the EcoR1 F' (or F::Tn916) from pAD1. The shuttle also has a marker conferring resistance to erythromycin. When introduced into Challis, the majority (greater than 90%) of the tetracycline resistant transformants are sensitive to erythromycin. When chromosomal DNA is probed for the presence of Tn916, the transposon can be observed at various locations. In the case of tetracycline resistant transformants that are also resistant to erythromycin, plasmid DNA is present but no longer contain Tn916. Rather, the EcoR1 fragment F is present in place of the F'.

This work not only indicates Tn916 excises upon introduction into the cell, but that a plasmid such as pAM118 can be used as a delivery system for insertional mutagenesis in transformable bacteria. The high frequency of excision in S. sanguis also offers this system as a possible alternative to E. coli for cloning.

In similar manner, other conjugative transposons have been shown to behave like Tn916. Tn918 was discovered in S. faecalis RC73, a hemolytic, Tc-resistant clinical isolate obtained from University Hospital (Ann Arbor) [Clewell et al, J. Bacteriol. 162:1212 (1985)]. The strain harbors at least five plasmids and was of interest because it contained a conjugative plasmid, pAM373, which determined a pheromone-related mating response when exposed to recipient cells. An activity resembling the pheromone, cAM373, appeared to be also produced by numerous strains of Staphylococcus aureus and some strains of Streptococcus sanguis. When the conjugal transfer of RC73's Tc-resistance was selected for in mating with an appropriate S. faecalis recipient, the tet determinant could in some cases by found inserted into pAM373 or into the recipient chromosome. Being able to subsequently transfer conjugatively in the absence of plasmid DNA, tet proved to be a conjugative transposon with properties resembling Tn916 [Clewell et al, J. Bacteriol. 162:1212 (1985)].

Tn918 was able to insert into pAD1 and give rise to hyperhemolytic derivatives in a manner essentially identical to that of Tn916. Southern blot hybridization analyses using Tn916 as a probe showed that the two transposons were highly homologous and were indistinguishable with respect to the size of their five internal HincII fragments. The size of Tn918 appeared identical to that of Tn916.

In connection with interests in determining if pAM373 would transfer from S. faecalis into S. aureus, derivatives of the plasmid carrying Tn918 (or Tn916) were used in mating experiments. The plasmid would not extablish in the S. aureus background, but it appeared to act as a suicide delivery vehicle for insertion of the transposon at different sites in the staphylococcal chromosome.

Tn919 is a conjugative transposon discovered in S. sanguis FC1 [Fitzgerald and Clewell, Infect. and Immunity, 47:415 (1985)]. It encodes Tc-resistance, and could be shown to transfer to S. faecalis and subsequently transpose to Pad', generating hyperhemolytic derivatives. Hybridization analyses with Tn916 showed strong homology and revealed four of the five internal HincII fragments being of similar size. A 4.2 kb HincII fragment in Tn919 was present in place of a 4.8 kb fragment in Tn916. This segment is believed to contain tet.

Both Tn918 and Tn919 could be cloned in E. coli and expressed Tc-resistance in the gram-negative background. Like Tn916, when present on the multicopy plasmid vector (pGL101) in E. coli, there was a very high degree of excision and segregation of the transposons.

S. faecalis RC73 and S. sanguis FC1 are maintained in vialbe form in the laboratory of Dr. Don B. Clewell at The University of Michigan and will be maintained and are available under the requirements of the U.S. Patent Laws.

Cultures of the new life forms made in accordance with this invention have been deposited with the following depositories and given the following accession numbers:

In Vitro International. Inc., 7885 Jackson Road, Ann Arbor, Mich. 48103 USA.

| Culture | Accession Number |
|---|---|
| S. faecalis DS16 | IVI-1326 |
| S. faecalis CG110 | IVI-1327 |
| S. faecalis DS16C3 | IVI-1328 |
| E. coli CG118 | IVI-1329 |
| E. coli CG120LT | IVI-1330 |
| E. coli CG170LT | IVI-1331 | and with the Agricultural Research Culture Collection (NRRL) 1815 North University Street, Peoria, Ill. 61604 USA.

| Culture | Accession Number |
|---|---|
| S. faecalis DS16 | NRRL-B-15411 |
| S. faecalis CG110 | NRRL-B-15412 |
| S. faecalis DS16C3 | NRRL-B-15410 |
| E. coli CG118 | NRRL-B-15413 |
| E. coli CG120LT | NRRL-B-15414 |
| E. coli CG170LT | NRRL-B-15415 |

The following example is given to further describe our invention, however, it is given for purposes of illustration and it not intended to limit the scope of our invention except as defined in the appended claims.

EXAMPLE

A concise example of the process is the cloning in *E. coli* of the EcoR1 F' restriction fragment of the *S. faecalis* plasmid pAM211 (PAD1::Tn916). Tn916 had been inserted into the EcoR1 F fragment of PAD1 to give rise to pAM211. The EcoR1 F' fragment (i.e. F::Tn916) was purified by electroeluting the DNA from an agarose gel slice and ethanol precipitation, see Gawron-Burke and Clewell, Nature, 300:281, (1982). The purified EcoR1 F' fragment (0.5 micrograms) was ligated to 3 micrograms of alkaline phosphatase-treated EcoR1-digested pGL101 (a derivative of pBR322 encoding ampicillin-resistance (Ap) see Lauer, et. al., J. Molec. and Applied Genet., 1:139, (1981). Conditions for alkaline phosphatase (Boehringer-Mannheim)-treatment of plasmid DNA and ligation with T4 DNA ligase (Bethesda Research Laboratories) were as described by Macrina et. al., J. Bacteriol., 143: 1425, (1980). This ligation mix was used to transform *E. coli* strain DH1 as detailed by Davis et. al., (Manual for Genetic Engineering: Advanced Bacterial Genetics, Cold Spring Harbor Laboratory, Cold Spring Harbor, N.Y., 1980), except that cells were harvested at an optical density of 0.2 (at 660 nm). Ap and Tc-resistant clones were selected on LB plates containing ampicillin (25 micrograms/ml) and tetracycline (4 micrograms/ml) and arose at low frequency (16 transformants/microgram of vector DNA). EcoR1-digested plasmid DNA from such clones (subsequently grown in the presence of 2.5 micrograms/ml Tc displayed the expected restriction pattern of the cloned EcoR1 F' fragment and a single EcoR1 fragment corresponding to the pGL101 vector when subjected to agarose gel electrophoresis (see FIG. 4). EcoR1-digested plasmid DNA isolated from Ap and Tc resistant clones grown in the absence of Tc displayed a restriction pattern as shown in FIG. 4 consisting of the pGL101 vector fragment and a fragment co-migrating with the EcoR1 F fragment of pAD1. That the fragment was indeed EcoR1 F of pAD1 was confirmed in Southern blot hybridization experiments in which EcoR1-digested pAD1 plasmid DNA was probed with P32-labeled plasmid DNA isolated from clones grown in the absence of Tc.

In accordance with our invention although the microorganisms which may be employed are varied in structure including bacteria, algae, fungi, protozoa and bacteriophage, we have had best results employing bacteria, either Gram negative or Gram positive and especially bacteria of the genus Streptococcus.

The process and new life forms of this invention are useful for producing various products. For example, the genetic determinants for the Streptococcal Group A M-protein, erythrogenic toxins, or streptokinase can be cloned using this process. The genetic determinants of *S. mutans* involved in cariogenicity can be cloned using this process. The cloning of the genes encoding the glucosyltransferases or the surface proteins involved in adherence to the tooth surface and adjacent bacteria would be an important step in the development of a vaccine for dental caries. The process of this invention could be used to clone insecticidal toxins produced by a variety of species of Bacillus.

An "excising transposon" as used herein means a transposon whose mechanism of transposition involves an excision step; and the excision step occurs at a high frequency in a host-vector system as exemplified by Tn916.

The work done herein was all done in conformity with the physical and biological containment requirements specified in the guidelines published by the National Institutes of Health, Washington, D.C., USA.

Although our invention has been described using specific examples and certain preferred embodiments thereof, we do not intend that our invention be limited in scope except as expressly defined in the appended claims.

We claim:
1. A process for cloning a gene which comprises,
   (1) introducing excising transposon Tn 916 by transformation, conjugation, or transduction into a host microorganism which comprises a gene which is to be cloned,
   (2) selecting for the transformed microorganisms which comprise Tn 916 inserted into said gene as evidenced by the insertional inactivation of the phenotype encoded for by said gene,
   (3) isolating the DNA which contains Tn 916 from said selected transformed microorganisms,
   (4) cleaving said isolated DNA with a suitable restriction enzyme so as to leave the Tn 916 and the gene intact,
   (5) ligating said cleavage DNA fragment which comprises the Tn 916 and the cloned gene to a vector,
   (6) introducing the chimaeric DNA produced in step (5) into a host microorganism by transformation,
   (7) selecting for the transformed microorganisms which comprise said chimaeric DNA by screening for tetracycline resistance, and
   (8) culturing said selected transformed microorganism in the absence of tetracycline so as to excise Tn 916 from said chimaeric DNA and thereby restore the phenotypical trait encoded for by the cloned gene.

2. A process for cloning a gene which comprises,
   (1) introducing excising transposon Tn 916 by transformation, conjugation, or transduction into a bacteria which comprises a gene which is to be cloned,
   (2) selecting for the transformed bacteria which comprise Tn 916 inserted into said gene as evidenced by the insertional inactivation of the phenotype encoded for by said gene,
   (3) isolating the DNA which contains Tn 916 from said selected transformed bacteria,
   (4) cleaving said isolated DNA with a suitable restriction enzyme so as to leave the Tn 916 and the gene intact,
   (5) ligating said cleavage DNA fragment which comprises the Tn 916 and the cloned gene to a vector,
   (6) introducing the chimaeric DNA produced in step (5) into a bacteria by transformation,
   (7) selecting for the transformed bacteria which comprise said chimaeric DNA by screening for tetracycline resistance, and
   (8) culturing said selected transformed bacteria in the absence of tetracycline so as to excise Tn 916 from said chimaeric DNA and thereby restore the phenotypical trait encoded for by the cloned gene.

3. The process of claim 2 wherein the bacteria is the genus Bacillus.

4. The process of claim 2 wherein the bacteria is the genus Streptococcus.

5. The process of claim 2 wherein the bacteria is the genus Streptomyces.

6. The process of claim 2 wherein the species is *Streptococcus mutans*.

7. The process of claim 2 wherein the species is *Streptococcus faecalis*.

8. The process of claim 2 wherein the bacteria is *Streptococcus faecalis*, the restriction enzyme is EcoR1, the plasmid vector is PGL101, and the host is *E. coli*.

* * * * *